United States Patent [19]
Pellico et al.

[11] Patent Number: 4,578,265
[45] Date of Patent: * Mar. 25, 1986

[54] DI-ENZYMATIC DENTIFRICE

[75] Inventors: Michael A. Pellico; Robert E. Montgomery, both of Los Angeles, Calif.

[73] Assignee: Laclede Professional Products, Inc., Gardena, Calif.

[*] Notice: The portion of the term of this patent subsequent to May 26, 1998 has been disclaimed.

[21] Appl. No.: 292,633

[22] Filed: Aug. 13, 1981

[51] Int. Cl.$^4$ .................. A61K 7/28; A61K 37/48
[52] U.S. Cl. .................................. 424/50; 424/94
[58] Field of Search .................. 424/129, 49–58, 424/94

[56] References Cited

U.S. PATENT DOCUMENTS

| | | | |
|---|---|---|---|
| 1,169,998 | 2/1916 | Rhodes | 424/49 |
| 1,739,586 | 12/1929 | Gerngross et al. | 424/129 |
| 1,740,543 | 12/1929 | Gerngross et al. | 424/129 |
| 4,012,839 | 3/1977 | Hill | 424/129 |
| 4,150,113 | 4/1979 | Hoogendoorn et al. | 424/50 |
| 4,178,362 | 12/1979 | Hoogendoorn et al. | 424/50 |
| 4,269,822 | 5/1981 | Pellico et al. | 424/50 |
| 4,320,116 | 3/1982 | Bjorck | 424/129 |

*Primary Examiner*—Shep K. Rose
*Attorney, Agent, or Firm*—Donald Diamond

[57] ABSTRACT

A di-enzymatic dentifrice is provided which contains an oxidizable substrate and an oxidoreductase enzyme specific to such substrate for producing hydrogen peroxide upon oral application of the dentifrice and further contains a thiocyanate salt and lactoperoxidase for interacting with hydrogen peroxide to produce a hypothiocyanate bacterial inhibitor. An illustrative enzymatic system for this purpose contains glucose, glucose oxidase, potassium thiocyanate and lactoperoxidase.

17 Claims, No Drawings

DI-ENZYMATIC DENTIFRICE

BACKGROUND OF THE INVENTION

This invention relates to dentifrice compositions and, more particularly, to antiseptic dentifrice compositions wherein hypothiocyanate, a bacterial inhibitor, is produced in situ during oral application of the dentifrice.

Dentifrices, in powder, paste, cream and liquid forms, are used for both cosmetic and therapeutic purposes. Consistent with these purposes, dentifrices are formulated to contain active ingredients such as cleansing and polishing materials, as well as various antibacterial and anticaries agents for use as aids in the prevention of tooth decay.

It is generally understood in the dental art that certain kinds of tooth decay are initiated by acid etching of the tooth enamel with the source of the acid being a metabolite resulting from bacterial and enzymatic action on food particles in the oral cavity. It is generally accepted that plaque—which is a soft accumulation on the tooth surfaces consisting of an organized structure of microorganisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associates with the plaque cause decalcification beneath the plaque matrix through metabolic activity which results in the accumulation and localized concentration of organic acids. The etching and decalcification of the enamel may continue until the pulp chamber of the tooth is reached.

A wide variety of materials have been considered for use as decay-preventative agents in dentifrice compositions. Some of the substances which have been so considered include para-aminobenzoic acid, a combination of urea and urease to produce ammonia during oral application of the dentifrice, chlorophyll, perfluorinated long chain organic compounds, complex iodine, penicillin, benzohydroxamic acid, and glucose oxidase to produce hydrogen peroxide during oral application of the dentifrice.

U.S. Pat. No. 2,526,614 (Butterfield, 1950) discloses the incorporation into a dentifrice of an enzyme system comprising urea and urease which produces ammonia in the presence of moisture that is encountered during oral application of the dentifrice. The patentee reports that the action of the ammonia together with residual urea is bacterocidal to acidogenic organisms and antienzymatic to the production of lactic acid by such organisms. In addition, it is pointed out that the action of ammonia produced from this enzyme system dissolves mucin plaques.

U.S. Pat. No. 3,427,380 (Kirkland, 1969) discloses that oral organisms produce a capsular material which is a factor in holding plaque together and allowing its further growth and that the oral application of a dentifrice containing para-aminobenzoic acid inhibits capsule formation by such organisms and thereby retards the development of dental plaque without inhibiting the growth of these organisms.

U.S. Pat. No. 3,137,634 (Schiraldi, 1964) discloses that the oral application of a dentifrice composition containing, for example, potassium copper chlorophyllin, dicalcium phosphate dihydrate, and tetrasodium pyrophosphate is useful in the treatment of gum diseases such as periodontal disorders like gingivitis, pyorrhea and trench mouth and, in addition, reduces undesirable breath odors.

U.S. Pat. No. 3,227,618 (Dunellen, 1966) in the background portion of the specification, recites that it has been disclosed that treatment of tooth enamel with a mixture of stannous flouride, hydrogen peroxide and insoluble sodium metaphosphate increases the enamel hardness as described in The Journal of the American Dental Association, May, 1950, Vol. 40, pg. 513-519.

Merck Index, 9th Edition, 1976, at page 633, discloses that hydrogen peroxide solution 3% contains 2.5-3.5 wt.% of hydrogen peroxide which is equivalent to 8-12 volumes of oxygen, and that this solution is a topical anti-infective which is useful in pharmaceutical preparations such as mouthwashes, dentifrices, and sanitary lotions.

U.S. Pat. No. 4,150,113, (Hoogendoorn et al, 1979) discloses an enzymatic dentifrice containing glucose oxidase which acts on glucose present in saliva and tooth plaque to produce hydrogen peroxide. The patentees, after noting that oral bacteria effect glycolysis of food products containing sugars through bacterial enzyme systems having SH-groups, point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al, 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

Morrison et al, Biology of the Mouth, American Association for the Advancement of Science, 1968, pp. 89-110 disclose that lactoperoxidase, sodium thiocyanate and hydrogen peroxide define an enhanced bacterial inhibitory system.

Hoogendoorn et al, Caries Research, 11:77-84, 1977, disclose that the hypothiocyanate ion is the bacterial inhibitor formed by the system containing lactoperoxidase, thiocyanate and hydrogen peroxide.

Thomas et al, Journal of Dental Research 60(4), pp. 785-796, April, 1981, disclose that the yield or accumulation of hypothiocyanate from the antimicrobial system containing lactoperoxidase, thiocyanate and hydrogen peroxide can be increased by the presence of aminohexoses, namely, glucosamine and N-acetyl glucosamine.

The effectiveness of a glucose oxidase dentifrice (U.S. Pat. No. 4,150,133) as a bacterial inhibitor through the production of hypothiocyanate is dependent, to a significant extent, upon the subsisting oral concentration of glucose, potassium thiocyanate and lactoperoxidase as well as hydrogen peroxide at the time of oral application. The concentration of those ingredients supplied by saliva, including potassium thiocyanate and lactoperoxidase, varies as a direct function of psysiological production and salivary flow. Thus, when salivary flow is at a diminished level either as a natural event or as a event arising out of certain types of medical treatment, the oral concentration of potassium thiocyanate and lactoperoxidase will be correspondingly reduced which, in turn, is a limiting factor in the oral production of hypothiocyanate bacterial inhibitor. Accordingly, it would be advantageous to provide a substantially self-contained, hypothiocyanate generating, engymatic dentifrice which is not dependent upon the naturally occurring, oral concentration of glucose, potassium thiocyanate or lactoperoxidase for antibacterial effectiveness, upon oral application of the dentifrice.

SUMMARY OF THE INVENTION

In accordance with the invention, there is provided a di-enzymatic dentifrice containing from about 0.015 to about 0.6 millimole of oxidizable substrate and from about 0.5 to about 500 International Units of an oxidoreductase enzyme specific to such substrate for producing hydrogen peroxide upon oral application of said dentrifice and further containing from about 0.0001 to about 0.01 millimole of a thiocyanate salt and from about 0.05 to about 20 International Units of lactoperoxidase for interacting with hydrogen peroxide to produce a hypothiocyanate bacterial inhibitor, wherein each of the aforesaid quantities is based upon one gram of dentifrice; and limiting any water present to an amount not more than about 10 wt. % based on the dentifrice weight to stabilize the dentifrice against the production of hydrogen peroxide prior to oral application of the dentifrice.

DETAILED DESCRIPTION

The di-enzymatic dentifrice of this invention comprises a first enzyme system containing an oxidizable substrate and an oxidoreductase enzyme specific to such substrate for producing hydrogen peroxide upon oral application of the dentifrice, with the chemical environment of the oral cavity providing the source of the additional reactant (oxygen) or reactants (oxygen, water) to effect the enzymatic reaction.

The components of the first enzyme system which can be incorporated into dentifrice compositions to produce hydrogen peroxide upon oral application of the dentifrice are illustrated by the substrate/enzyme combinations set forth in Table I.

TABLE I

| Oxidazable Substrate | Oxidoreductase Enzyme |
|---|---|
| (a) B-D-glucose | glucose oxidase |
| (b) D-galactose | galactose oxidase |
| (c) Urate | urate oxidase |
| (d) Choline | choline oxidase |
| (e) D-amino acids | D-amino acid oxidase |
| (f) D-glutamate | D-glutamate oxidase |
| (g) Glycine | glycine oxidase |
| (h) Glycollate | glyclollate oxidase |
| (i) L-sorbose | L-sorbose oxidase |
| (j) Primary alcohol | alcohol oxidase |
| (k) Primary amine | amine oxidase |

The reactions of representative enzyme systems from Table I, which are activated in the chemical environment of the oral cavity to produce hydrogen peroxide, are set forth in Table II.

TABLE II (a) Glucose oxidase catalyzes the interaction of Beta-D-glucose, water and oxygen to produce hydrogen peroxide and gluconic acid;

(b) Galactose oxidase catalyzes the interaction of D-galactose and oxygen to produce hydrogen peroxide and D-galacto-hexodialdose;

(c) Urate oxidase catalyzes the interaction of urate, water and oxygen to produce hydrogen peroxide, allantoin and carbon dioxide;

(d) Choline oxidase catalyzes the interaction of choline and oxygen to produce hydrogen peroxide and betaine aldehyde;

(e) D-amino acide oxidase catalyzes the interaction of D-amino acids such as the D isomers of proline, methionine, isoleucine, alanine, valine and phenylalanine together with water and oxygen to produce hydrogen peroxide, ammonia and the corresponding alpha-keto acids;

(f) D-glutamate oxidase catalyzes the interaction of D-glutamate, water and oxygen to produce hydrogen peroxide, ammonia and 2-oxoglutarate; and (g) Glycine oxidase catalyzes the interaction of glycine, water and oxygen to produce hydrogen peroxide, ammonia and glyoxylic acid.

The characteristics of representative oxidoreductase enzymes identified in Table I, from specific sources, are set forth in Table III.

TABLE III (a) Glucose oxidase from A. niger:
  (i) Molecular weight; 150,000 (Pazur et al., 1965); 153,000 (Swoboda, 1969).
  (ii) Composition: a glycoprotein containing two molecules of flavine-adenine dinucleotide (see: The Merck Index, 9th Ed., 1976, page 532, section 4007 and page 576, section 4291). The amino acid composition has been determined (Pazur et al., 1965).
  (iii) Ioselectric point: pH 4.2.
  (iv) Optimum pH: 5.5 with a broad pH range from 4 through 7.
  (v) Inhibitors: monovalent silver and divalent mercury and copper ions.

(b) Galactose oxidase from Dactylium Dendroides:
  (i) Molecular Weight: 42,000 (Kelly-Falcoz, 1965)
  (ii) Composition: metaloenzyme containing 1 gram atom of copper per mole (Amaral et al., 1963). The amino acid composition has been determined (Kelly-Falcoz, 1965).
  (iii) Optimum pH: 7 (Cooper et al., 1959).

(c) Urate oxidase (uricase) from hog liver or beef liver:
  (i) Molecular Weight: 100,000 (Mahler et al., 1955).
  (ii) Composition: metaloenzyme containing 1 gram atom of copper per mole (Mahler, 1955).
  (iii) Isoelectric point: pH 6.3.
  (iv) Optimum pH: 9.

(e) D-Amino Acid Oxidase from Hog Kidney:
  (i) Molecular Weight: 90,000 (Antonini et al., 1966).
  (ii) Composition: A glycoprotein containing two molecules of flavine-adenine dinucleotide.
  (iii) Optimum pH: 9.
  (iv) Inhibitors: certain heavy metals.

The oxidizable substrate is generally present in the dentifrice in an amount from about 0.015 to about 0.6 millimole per gram of dentifrice and, preferably, from about 0.025 to about 0.1 millimole per gram of dentifrice while the oxidoreductase enzyme specific to the substrate is generally present in the dentifrice in an amount from about 0.5 to about 500 International Units (hereinafter sometimes abbreviated IU) per gram of dentifrice and preferably, from about 10 to about 40 IU per gram of dentifrice. The term millimole identifies that quantity in grams corresponding to the molecular weight of the composition divided by one thousand. The term International Unit(s) identifies that amount of enzyme that will effect catalysis of 1.0 micromole of substrate per minute at pH 7.0 and 25° C. Oxidoreductase enzymes are supplied in dry or liquid form with the label specifying the concentration in International Units on a per gram or per milliliter basis, as appropriate.

In addition to the first enzyme system comprising oxidizable substrate and oxidoreductase enzyme specific to such substrate for producing hydrogen peroxide, the di-enzymatic dentifrice of this invention is provided with a second enzyme system containing a thiocyanate salt and lactoperoxidase for interacting with hydrogen peroxide to produce a bacterial inhibitor in the form of a negative, monovalent hypothiocyanate ion (OSCN) which exists in solution in an equilibrium with its corresponding salt such as potassium hypothiocyanate (KOSCN).

The thiocyanate salts which can be used in the dentifrice include sodium thiocyanate, potassium thiocyanate, ammonium thiocyanate, ferric thiocyanate, cuprous thiocyanate and mixtures thereof. The thiocyanate salt is generally present in the dentifrice in an amount from about 0.0001 to about 0.01 millimole per gram of dentifrice and, preferably, from about 0.001 to about 0.006 millimole per gram of dentifrice.

Lactoperoxidase is a glycoprotein which, in one commercial embodiment, is a lyophilized powder derived from milk. This commercial peroxidase has an activity of 80 IU/mg and a projected molecular weight of 93,000 for L-Tyrosine Iodination. The physical-chemical properties reported for lactoperoxidase include: molecular weight 78,000; partial specific volume 0.74; and heme/mole 1.0. Lactoperoxidase is generally present in the dentifrice in an amount from about 0.05 to about 20 IU per gram of dentifrice and, preferably, in an amount from about 0.1 to about 1.0 IU per gram of dentifrice.

The di-enzymatic dentifrice of this invention may advantageously be formulated with an aminohexose as, for example, an aminoglucose such as glucosamine, N-acetyl N-acetyl glucosamine or mixtures thereof in order to increase the yield or accumulation of the hypothiocyanate ion. The aminoglucose is generally present in the dentifrice in an amount from about 0.001 to about 0.002 millimole per gram of dentifrice and, preferably, in an amount from about 0.003 to about 0.001 millimole per gram of dentifrice.

Since water promotes the oxidation/reduction reactions of this invention and is also a reactant in certain reactions, the use of water in formulating the dentifrice compositions should be at a relatively low concentration level in order to impart maximum stability and shelf life to the compositions. For this purpose, it has been found to be essential to limit any water present in the dentifrice to an amount not more than about 10 wt. %. In view of this water limitation, a non-aqueous fluid carrier is advantageously employed in the toothpaste formulation so as to provide the formulation with pressure responsive flow characteristics. Any suitable non-aqueous fluid may be used for this purpose. Organic fluid carriers, such as glycerine or propylene glycol provide a stable toothpaste environment for the enzyme systems of this invention. The non-aqueous fluid carrier is generally present in the dentifrice composition in an amount from about 30 to about 60 wt.% and, preferably, in an amount from about 45 to about 55 wt.%.

Where the products of the activated enzyme system include a weak organic acid, it is advantageous to formulate the dentifrice with a buffering agent to neutralize the organic acid. A suitable buffering agent is sodium bicarbonate which can be present in the dentifrice in an amount up to about 6 wt.% as, for example, in an amount from about 4 to about 6 wt.%.

Dentifrices, especially toothpaste, are preferred oral compositions for the purpose of this invention. Dentifrice compositions typically contain an abrasive polishing material and a surfactant as well as flavoring, sweetening and coloring agents. Toothpaste usually also contains humectants and thickeners.

Any abrasive polishing material which does not excessively abrade dentin and is compatible with the oxidoreductase enzymes described herein can be used in the compositions of this invention. These include, for example, calcium carbonate, calcium pyrophosphate, dicalcumium phosphate, zirconium oxide and aluminum oxide. The abrasive polishing material is usually present in toothpaste in an amount from about 20 to 60 wt.%.

The surfactants which can be used are those which yield substantial levels of foam and which are otherwise acceptable for use in the oral cavity and compatable with the oxidoreductase enzymes. A suitable surfactant is sodium lauryl sulfate. However, a protein surfactant or dioctyl sodium sulfosuccinate surfactant is preferred because these surface active materials have been found to be more compatible with the oxidoreductase enzymes. The surfactants can be employed at concentration levels ranging from about 0.5 to about 5.0 wt.%.

The di-enzymatic dentifrice, in the form of a toothpaste, can be prepared in any suitable manner as, for example, by blending the dry ingredients into the liquid ingredients, with agitation, until a smooth mixture is obtained. The addition of any surfactant to the mixture should take place as the last step in order to minimize foaming of the batch.

EXAMPLES

The following examples further illustrate the compositions of this invention. The term "Maypon" used in the examples is the trademark of Stepan Chemical Company, Fieldsboro, N.J., for a potassium coco condensate of hydrolyzed animal protein having a molecular weight between 750 and 1,500 and supplied as an aqueous solution containing 34 to 40% solids. The term "Super-Pro" used in the examples is the trademark of Stepan Chemical Company for an aqueous solution of sorbitol and triethanolamine condensate of hydrolyzed animal protein having a molecular weight between 750 and 1,500 with the solution having a solids content from 62–70%. The term "DSS" used in the examples is the abbreviation for dioctyl sodium sulfosuccinate. Distilled water is employed in the examples.

The term "Silcron G-910"0 used in the examples is the trademark of SCM/Glidden for a polishing agent comprising a micron-sized hydrated silica gel.

EXAMPLE 1

This example compares the antibacterial properties of a di-enzymatic toothpaste of this invention containing glucose, glucose oxidase, potassium thiocyanate and lactoperoxidcase with the antibacterial properties of an enzymatic toothpaste containing glucose oxidase alone as taught in U.S. Pat. No. 4,150,113 (Hoogendorn, 1979).

Enzymatic toothpastes were prepared having the following formulations:

| Composition | Weight, grams | |
|---|---|---|
| | 1A | 1B |
| Glycerine (99%) | 48 | 48 |
| Propylene glycol | 5 | 5 |
| Sodium bicarbonate | 1.9 | 1.9 |
| Silcron G-910 | 35 | 35 |
| Water | 2 | 2 |
| DSS | 2 | 2 |
| Glucose oxidase (100,000 IU/g) | 0.125 g (12,500 IU) | 0.125 g (12,500 IU) |
| Beta-D-glucose | 5 | |
| Lactoperoxidase (100,000 IU/g) | 0.001 g (10 IU) | |
| Potassium thiocyanate | 0.01 | |
| Color | 0.5 | 0.5 |
| Flavor | 0.5 | 0.5 |

In the above formulations, Composition 1A corresponds to the instant invention while Composition 1B simulates the prior art. The compositions were prepared by blending the dry ingredients into the liquid ingredients, with agitation, until a smooth admixture was obtained.

Ten individuals rinsed their mouths for five minutes with an aqueous sugar solution containing 25 wt. % sucrose and 25 wt % glucose. The ten individuals were divided into five groups, with two persons to a group. Saliva samples were separately collected from the ten individuals in accordance with the following time sequence: group 1, immediately after rinsing; group 2, 60 minutes after rinsing; group 3, 120 minutes after rinsing; group 4, 180 minutes after rinsing; and group 5, 240 minutes after rinsing. One individual in each group was designated "A" and the other individual in each group was designated "B".

Ten bacterial specimens were prepared by pouring 10 ml of Brain-Heart Infusion agar containing 10,000 colony units of streptococcus mutans (strain C67-1) per ml into each of 10 Petri dishes, as needed, with one dish in each set of two dishes being designated "A" and the dish being designated "B".

Promptly following the collection of saliva from individuals "A" and "B" in each time period, 5 ml of salvia from individual "A" and 1.0 ml of Toothpaste Composition 1A were added with stirring to Petri dish "A" and 5 ml of saliva from individual "B" and 1.0 ml of Toothpaste Composition 1B were added with stirring to Petri dish "B". The resulting admixtures were incubated in an oven at 35° C. for 10 minutes. Upon completion of the incubation period, the bacterial specimen admixture were removed from the oven and microscopically evaluated for bacterial inhibition as determined by visibie colony count. The results of this comparative study are set forth in Table IV.

TABLE IV

| Group | Time, minutes after rinse when ingredients added to bacterial broth | Percent Bacterial Inhibition | |
|---|---|---|---|
| | | Saliva "A" Composition 1A | Saliva "B" Composition 1B |
| 1 | immediately | 99 | 99 |
| 2 | 60 | 99 | 78 |
| 3 | 120 | 99 | 59 |
| 4 | 180 | 99 | 42 |
| 5 | 240 | 99 | 38 |

Since glucose concentration in the oral cavity decreases with increasing time lapse following a sugar rinse, the results set forth in Table IV show that the di-enzymatic compositions of this invention maintain significant antibacterial effectiveness in an oral environment of declining glucose concentration whereas the antibacterial effectiveness of enzymatic compositions of the prior art containing glucose oxidase as the essential active ingredient decrease with declining glucose concentration.

EXAMPLE 2

The following examples show varying ingredients and concentration levels which can be used in the preparation of di-enzymatic toothpaste compositions.

2A

| Composition | weight, grams |
|---|---|
| Glycerine (99%) | 50 |
| Calcium pyrophosphate | 40 |
| Sodium bicarbonate | 5 |
| Water | 1.5 |
| Super-Pro | 2 |
| Glucose oxidase (100,000 IU/g) | 0.1 (10,000 IU) |
| Beta-D-glucose | 0.5 |
| Lactoperoxidase (100,000 IU/g) | 0.002 (200 IU) |
| Sodium thiocyanate | 0.04 |
| Color | 0.5 |
| Flavor | 0.5 |

2B

| Composition | weight, grams |
|---|---|
| Glycerine (99%) | 47 |
| Calcium pyrophosphate | 40 |
| Titanium dioxide | 5 |
| Water | 3 |
| Sodium lauryl sulphate | 2 |
| Glucose oxidase (100,000 IU/g) | 0.4 (40,000 IU) |
| Beta-D-glucose | 2 |
| Lactoperoxidase (100,000 IU/g) | 0.008 (800 IU) |
| Potassium thiocyanate | 0.002 |
| Color | 0.5 |
| Flavor | 0.5 |

2C

| Composition | weight, grams |
|---|---|
| Glycerine (99%) | 50 |
| Calcium pyrophosphate | 40 |
| Sodium bicarbonate | 5 |
| Water | 1.5 |
| D-amino acid oxidase (100,000 IU/g) | 0.1 (10,000 IU) |
| D-alanine | 0.5 |
| Lactoperoxidase (100,000 IU/g) | 0.002 (200 IU) |
| Sodium thiocyanate | 0.04 |
| Color | 0.5 |
| Flavor | 0.5 |

2D

| Composition | weight, grams |
|---|---|
| Glycerine (99%) | 46 |
| Titanium dioxide | 2 |
| Silcron G-910 | 40 |
| Water | 2 |
| Maypon | 2 |
| Glucose oxidase (100,000 IU/g) | 0.05 (5,000 IU) |
| Beta-D-glucose | 1 |
| Lactoperoxidase (100,000 IU/g) | 0.01 (1,000 IU) |
| Potassium thiocyanate | 0.005 |
| Color | 0.5 |

-continued

| Composition | weight, grams |
|---|---|
| Flavor | 0.5 |

2E

| Composition | weight, grams |
|---|---|
| Glycerine (99%) | 46 |
| Titanium dioxide | 2 |
| Silcron G-910 | 40 |
| Water | 2 |
| Maypon | 2 |
| D-glutamate oxidase (100,000 IU/g) | 0.05 (5,000 IU) |
| D-glutamate | 1 |
| Lactoperoxidase (100,000 IU/g) | 0.01 (1,000 IU) |
| Sodium thiocyanate | 0.08 |
| Color | 0.5 |
| Flavor | 0.5 |

2F

| Composition | weight, grams |
|---|---|
| Propylene glycol | 48 |
| Dicalcium phosphate | 45 |
| Water | 3.5 |
| Super-Pro | 2 |
| Glucose oxidase (100,000 IU/g) | 0.0008 (80 IU) |
| Beta-D-glucose | 0.5 |
| Lactoperoxidase (100,000 IU/g) | 0.005 (500 IU) |
| Sodium thiocyanate | 0.01 |
| Color | 0.5 |
| Flavor | 0.5 |

2G

| Composition | weight, grams |
|---|---|
| Glycerine (99%) | 50 |
| Calcium pyrophosphate | 40 |
| Dicalcium phosphate | 5 |
| Water | 2 |
| Glucose oxidase (100,000 IU/g) | 0.05 (5,000 IU) |
| Beta-D-glucose | 1 |
| Choline oxidase (100,000 IU/g) | 0.02 (2,000 IU) |
| Choline | 1 |
| Lactoperoxidase (100,000) IU/g) | 0.008 (800 IU) |
| Potassium thiocyanate | 0.009 |
| Color | 0.5 |
| Flavor | 0.5 |

2H

| Composition | weight, grams |
|---|---|
| Glycerine (99%) | 42 |
| Dicalcium phosphate | 6 |
| Titanium dioxide | 2 |
| Silcron G-910 | 38 |
| Water | 5 |
| Glucose oxidase (100,000 IU/g) | 0.4 (40,000 IU) |
| Beta-D-glucose | 6 |
| Lactoperoxidase (100,000 IU/g) | 0.001 (100 IU) |
| Sodium thiocyanate | 0.01 |
| Color | 0.5 |
| Flavor | 0.5 |

2I

| Composition | weight, grams |
|---|---|
| Glycerine (99%) | 42 |
| Dicalcium phosphate | 6 |
| Titanium dioxide | 2 |
| Silcron G-910 | 38 |
| Water | 5 |
| Glucose oxidase (100,000 IU/g) | 0.02 (2,000 IU) |
| Beta-D-glucose | 1 |
| Lactoperoxidase (100,000 IU/g) | 0.001 (100 IU) |
| Sodium thiocyanate | 0.01 |
| Color | 0.5 |
| Flavor | 0.5 |

2J

| Composition | weight, grams |
|---|---|
| Glycerine (99%) | 50 |
| Titanium dioxide | 2 |
| Silcron G-910 | 40 |
| Water | 2 |
| Super-Pro | 2 |
| Glucose oxidase (100,000 IU/g) | 0.02 (2,000 IU) |
| Beta-D-glucose | 2 |
| Lactoperoxidase (100,000 IU/g) | 0.01 (1,000 IU) |
| Sodium thiocyanate | 0.01 |
| Color | 0.5 |
| Flavor | 0.5 |

2K

| Composition | weight, grams |
|---|---|
| Propylene glycol | 44 |
| Sodium bicarbonate | 5 |
| Silcron G-910 | 40 |
| Water | 6.4 |
| Super-Pro | 2 |
| Glucose oxidase (100,000 IU/g) | 0.025 (2,500 IU) |
| Beta-D-glucose | 1.5 |
| Lactoperoxidase (100,000 IU/g) | 0.006 (600 IU) |
| Potassium thiocyanate | 0.005 |
| Color | 0.5 |
| Flavor | 0.5 |
| N—acetyl glucosamine | 0.15 |

2L

| Composition | weight, grams |
|---|---|
| Propylene glycol | 48 |
| Sodium bicarbonate | 5 |
| Silcron G-910 | 40 |
| Water | 2.4 |
| Super-Pro | 2 |
| Glucose oxidase (100,000 IU/g) | 0.025 (2,500 IU) |
| Beta-D-glucose | 1.5 |
| Lactoperoxidase (100,000 IU/g) | 0.0005 (50 IU) |
| Potassium thiocyanate | 0.005 |
| Color | 0.5 |
| Flavor | 0.5 |
| Glucosamine | 0.1 |

2M

| Composition | weight, grams |
|---|---|
| Glycerine (99%) | 47 |
| Sodium bicarbonate | 5 |
| Silcron G-910 | 40 |

| Composition | weight, grams |
| --- | --- |
| Water | 3.5 |
| Super-Pro | 2 |
| Glucose oxidase (100,000 IU/g) | 0.04 (4,000 IU) |
| Beta-D-glucose | 1.5 |
| Lactoperoxidase (100,000 IU/g) | 0.012 (1,200 IU) |
| Sodium thiocyanate | 0.05 |
| Color | 0.5 |
| Flavor | 0.5 |
| Glucosamine | 0.012 |
| N—acetyl glucosamine | 0.01 |

In view of the foregoing description and examples, it will become apparent to those of ordinary skill in the art that equivalent modifications thereof may be made without departing from the spirit and scope of this invention.

That which is claimed is:

1. A di-enzymatic dentifrice containing from about 0.015 to about 0.6 millimole of oxidizable substrate and from about 0.5 to about 500 International Units of an oxidoreductase enzyme specific to such substrate for producing hydrogen peroxide upon oral application of said dentifrice and further containing from about 0.0001 to about 0.01 millimole of a thiocyanate salt and from about 0.05 to about 20 International Units of lactoperoxidase for interacting with hydrogen peroxide to produce a hypothiocyanate bacterial inhibitor, wherein each of the aforesaid quantities is based upon one gram of dentifrice; and limiting any water present in the dentifrice to an amount not more than about 10 wt. % based on the dentifrice weight to stabilize the dentifrice against the production of hydrogen peroxide prior to the oral application of the dentifrice.

2. The dentifrice of claim 1 wherein the oxidizable substrate is Beta-D-glucose and the oxidoreductase enzyme is glucose oxidase.

3. The dentifrice of claim 1 wherein the oxidizable substrate is D-galactose and the oxidoreductase enzyme is galactose oxidase.

4. The dentifrice of claim 1 wherein the oxidizable substrate is urate and the oxidoreductase enzyme is urate oxidase.

5. The dentifrice of claim 1 wherein the oxidizable substrate is choline and the oxidoreductase enzyme is choline oxidase.

6. The dentifrice of claim 1 wherein the oxidizable substrate is a D-amino acid selected from the group consisting of D isomers of proline, methionine, isoleucine, alanine, valine and phenylalanine and the oxidoreductase enzyme is D-amino acid oxidase.

7. The dentifrice of claim 1 wherein the substrate is D-glutamate and the oxidoreductase enzyme is D-glutamate oxidase.

8. The dentifrice of claim 1 wherein the oxidizable substrate is glycine and the oxidoreductase enzyme is glycine oxidase.

9. The dentifrice of claim 1 wherein the thiocyanate salt is a member selected from the group consisting of sodium thiocyanate, potassium thiocyanate, ammonium thiocyanate and mixture thereof.

10. The dentifrice of claim 1 which also contains an aminoglucose selected from the group consisting of glucosamine, N-acetyl glucosamine and mixture thereof in an amount from about 0.001 to about 0.002 millimole per gram of dentrifrice.

11. The dentifrice of claim 1 wherein the oxidizable substrate is present in an amount from about 0.025 to about 0.1 millimole per gram of dentrifrice.

12. The dentifrice of claim 1 wherein the oxidoreductase enzyme is present is an amount from about 10 to about 40 International Units per gram of dentrifrice.

13. The dentifrice of claim 1 wherein the thiocyanate salt is present in an amount from about 0.001 to about 0.006 millimole per gram of dentrifrice.

14. The dentifrice of claim 1 wherein lactoperoxidase is present in an amount from about 0.1 to about 1.0 International Units per gram of dentrifrice.

15. The dentifrice of claim 9 wherein the aminoglucose is present in amount from about 0.0003 to about 0.001 millimole per gram of dentrifrice.

16. The dentifrice of claim 1 wherein the oxidizable substrate is glucose which is present in an amount from about 0.025 to about 0.1 millimole per gram of dentrifice, the oxidoreductase enzyme is glucose oxidase which is present in amount from about 10 to about 40 International Units per gram of dentrifrice, the thiocyanate salt is present in an amount from about 0.001 to about 0.006 millimole per gram of dentrifice, and lactoperoxidase is present in an amount from about 0.1 to about 1.0 International Unit per gram of dentrifice.

17. The dentifrice of claim 16 which also contains an aminoglucose selected from the group consisting of glucosamine, N-acetyl glucosamine and mixture thereof in an amount from about 0.0003 to about 0.001 millimole per gram of dentrifice.

* * * * *